(12) United States Patent
Ahonen et al.

(10) Patent No.: US 10,444,301 B2
(45) Date of Patent: Oct. 15, 2019

(54) APPARATUS AND A METHOD FOR HELIUM COLLECTION AND RELIQUEFACTION IN A MAGNETOENCEPHALOGRAPHY MEASUREMENT DEVICE

(71) Applicant: Megin Oy, Helsinki (FI)

(72) Inventors: Antti Ahonen, Helsinki (FI); Rob Blaauwgeers, Kauniainen (FI); Pasi Petteri Laine, Helsinki (FI); Sami Antero Lähteenmäki, Espoo (FI)

(73) Assignee: Megin Oy, Helsinki (FI)

( * ) Notice: Subject to any disclaimer, the term of this patent is extended or adjusted under 35 U.S.C. 154(b) by 251 days.

(21) Appl. No.: 15/518,138

(22) PCT Filed: Oct. 2, 2015

(86) PCT No.: PCT/IB2015/057549
§ 371 (c)(1),
(2) Date: Apr. 10, 2017

(87) PCT Pub. No.: WO2016/055915
PCT Pub. Date: Apr. 14, 2016

(65) Prior Publication Data
US 2017/0307698 A1 Oct. 26, 2017

(30) Foreign Application Priority Data

Oct. 9, 2014 (FI) .................................. 20145886

(51) Int. Cl.
*F17C 3/08* (2006.01)
*G01R 33/035* (2006.01)
(Continued)

(52) U.S. Cl.
CPC ...... *G01R 33/0354* (2013.01); *A61B 5/04008* (2013.01); *F17C 3/085* (2013.01);
(Continued)

(58) Field of Classification Search
CPC .... F17C 3/08; F17C 3/085; F17C 2227/0353; F17C 2227/0157; F17C 2250/0408;
(Continued)

(56) References Cited

U.S. PATENT DOCUMENTS 4,817,706 A   4/1989  Miyama et al.
5,293,750 A * 3/1994  Tamura .................. F17C 13/02
                                                      62/47.1
(Continued)

FOREIGN PATENT DOCUMENTS

EP   0 538 873 A1   4/1993
EP   0 544 943 A1   6/1993
(Continued)

OTHER PUBLICATIONS

Extended European Search Report for corresponding European Patent Application No. 15849658.8 dated Jun. 25, 2018, 8 pages.
(Continued)

*Primary Examiner* — Eric S Ruppert
(74) *Attorney, Agent, or Firm* — Merchant & Gould P.C.

(57) ABSTRACT

The invention relates to a method and a magnetoencephalography (MEG) measurement device. In the method there is determined the ending of a scheduled inactivity period of the MEG device. At the ending of the inactivity period a cryocooler of the MEG device is switched off. Helium is allowed to boil in the Dewar vessel of the MEG device when the MEG device is active and used to perform patient measurements. The boiled helium is collected via a compressor to an external storage tank. When a new inactivity period for the MEG device commences, the cryocooler is started anew and helium is let from the external storage tank in-to the Dewar vessel, where it is re-liquefied by the cryocooler. The compressor may be switched off when the cryocooler is switched on.

18 Claims, 4 Drawing Sheets

(51) Int. Cl.
　　*A61B 5/04*　　(2006.01)
　　*F25B 9/10*　　(2006.01)
(52) U.S. Cl.
　　CPC ........ *F25B 9/10* (2013.01); *A61B 2560/0242* (2013.01); *A61B 2560/0247* (2013.01); *A61B 2576/026* (2013.01); *F17C 2250/0673* (2013.01); *F17C 2265/034* (2013.01); *F17C 2270/0536* (2013.01); *F25B 2400/17* (2013.01)
(58) Field of Classification Search
　　CPC ..... F17C 2270/0527; F17C 2270/0536; G01R 33/3815; G01R 33/3804; H01F 6/04
　　See application file for complete search history.

(56) References Cited

U.S. PATENT DOCUMENTS

| | | |
|---|---|---|
| 5,713,354 A | 2/1998 | Warden |
| 5,782,095 A | 7/1998 | Chen |
| 6,332,324 B1 | 12/2001 | Saho et al. |
| 2004/0144101 A1 | 7/2004 | Hofmann |
| 2006/0137376 A1* | 6/2006 | Overweg ............. F25D 29/001 62/259.2 |
| 2006/0225437 A1 | 10/2006 | Kazami |
| 2008/0242974 A1 | 10/2008 | Urbahn et al. |
| 2009/0096452 A1 | 4/2009 | Gore et al. |
| 2012/0025821 A1* | 2/2012 | Strobel .................. F25B 9/145 324/307 |
| 2013/0014517 A1 | 1/2013 | Diederichs et al. |
| 2014/0232402 A1 | 8/2014 | Tsuda |

FOREIGN PATENT DOCUMENTS

| | | |
|---|---|---|
| EP | 1 591 062 A1 | 11/2005 |
| EP | 1 829 476 A1 | 9/2007 |
| JP | H11-99135 A | 4/1999 |
| JP | 2010-35596 A | 2/2010 |
| WO | WO 2013/010183 A1 | 1/2013 |

OTHER PUBLICATIONS

International Search Report for corresponding International Patent Application No. PCT/IB2015/057549 dated Feb. 16, 2016, 4 pgs.
Finnish Search Report for corresponding Finnish Patent Application No. 20145886 dated Jun. 3, 2015, 2 pgs.

\* cited by examiner

APPARATUS AND A METHOD FOR HELIUM COLLECTION AND RELIQUEFACTION IN A MAGNETOENCEPHALOGRAPHY MEASUREMENT DEVICE

This application is a National Stage Application of PCT/IB2015/057549, filed 2 Oct. 2015, which claims benefit of Ser. No. 20145886, filed 9 Oct. 2014 in Italy and which applications are incorporated herein by reference. To the extent appropriate, a claim of priority is made to each of the above disclosed applications.

BACKGROUND OF THE INVENTION

Field of the Invention

The invention relates to helium re-liquefaction. The invention relates to an apparatus and a method for helium collection and re-liquefaction in a magnetoencephalography measurement device.

Description of the Related Art

In Magnetoencephalography the magnetic fields generated by the brain activity of a patient are measured using Superconducting Quantum Interference Devices (SQUIDs), which are very sensitive magnetometers. The SQUID magnetometers require a working temperature close to 4 Kelvins. To achieve this working temperature, in a Magnetoencephalography (MEG) measuring device the SQUID magnetometers are placed inside a specially designed vacuum insulated Dewar vessel containing Liquid Helium (LHe). The SQUID magnetometers in the Dewar vessel are used to form a sensor assembly, which conforms to the shape of the patient's head. For the head there is an appropriately shaped helmet in the body of the Dewar vessel, in order to allow positioning of the sensor assembly as close to the patient's brains as possible. The helium in the Dewar vessel is liquefied elsewhere and transferred to the MEG measuring device using separate storage Dewar vessels and/or vacuum insulated transfer lines. In Magnetoencephalography the magnetic fields to be measured are extremely weak. In brains the magnetic fields are caused by a plurality of synchronized neuronal currents together inducing a net magnetic field that can be detected outside the patient's skull. The net magnetic field strength varies between 10 fT observed for cortical activity and 1000 fT observed for the alpha rhythm during wakeful relaxation with closed eyes of the patient. The weakness of the magnetic fields to be measured using a MEG measurement device is a problem when considering that there are usually several types of disturbing non-interesting magnetic fields which are due to interference sources at various distances from the MEG measurement device. The non-interesting magnetic fields may be due to, for example, supply lines for electrical power and a variety of electrical apparatuses. In order to alleviate the problem, the MEG measurement device is usually installed into a magnetically shielded room. The magnetically shielded room achieves a dampening of ambient magnetic fields outside the room, for example, by a factor of $10^2$ to $10^6$ depending on the oscillation frequency of the magnetic fields.

However, the magnetically shielded room does not help for interference sources located inside the magnetically shielded room. Examples of such interference sources include electrical apparatuses associated with the MEG measurement device itself. Liquid Helium (LHe) in the Dewar vessel boils off gradually due to the operating of the MEG measurement device and the thermal leakage into the Dewar vessel from the room temperature. The boiled helium may be lead outside the Dewar vessel and let into the atmosphere. This is not a preferable solution since helium is a scarce and costly resource. There is a problem if Helium needs to be re-liquefied in the Dewar vessel. The re-liquefying must be performed in the Dewar vessel in order to avoid using long Liquid Helium (LHe) supply lines, which are a complicated and an expensive solution. A solution is to have a cryocooler that liquefies helium directly into the Dewar vessel. The problem is that cryocoolers such as Gifford-McMahon cryocoolers, pulse tube cryocoolers, and Stirling cryocoolers cause electromagnetic interference which disturbs the measurement of weak interesting magnetic fields. It would be in principle possible to compensate in association with measurement signal processing for the electromagnetic noise caused by the cryocooler by utilizing knowledge of the electrical characteristics of the cryocoolers such as locations of the electrical wiring. However, such solutions are complicated, require large dynamic range of the SQUID sensors, and diminish the reliability of the magnetic field measurements of the MEG device. A further problem is the vibration caused by the mechanical movement of the displacer in the cold head of the GM cryocooler, or the operation of the rotary valve in the pulse-tube coolers. Similar mechanical movements are present in Stirling cryocoolers. Therefore, it would be beneficial to have a solution for re-liquefaction of helium which does not complicate MEG measurement result analysis and does not reduce the reliability of magnetic field measurements in a MEG measurement device.

SUMMARY OF THE INVENTION

According to an aspect of the invention, the invention is a magnetoencephalography measurement device, comprising: an assembly of a plurality of sensors placed in-side a Dewar vessel; the Dewar vessel, when in use, storing liquid helium to cool the assembly of sensors to a superconductive temperature, the Dewar vessel comprising a body portion, a mouth and a helmet portion formed in the body portion for receiving a patient's head, the assembly of sensors being arranged around the helmet portion inside the Dewar vessel; a cryocooler apparatus suspended inside the Dewar vessel; a lid sealing the mouth, the lid comprising a first orifice allowing a flow of helium gas from a storage tank to the Dewar vessel and allowing pumping of boiled helium gas to the storage tank from the Dewar vessel, when the Dewar vessel stores liquid helium and the storage tank stores helium gas; the storage tank in gaseous communication with the Dewar vessel via a line connected to the first orifice, when the Dewar vessel stores liquid helium and the storage tank stores helium gas, the line comprising a pressure controlling device; a compressor for pumping helium gas from the Dewar vessel to the storage tank, when the Dewar vessel stores liquid helium and the storage tank stores helium gas; a control unit comprising at least one processor and a memory storing instructions that, when executed, cause the control unit to switch the cryocooler apparatus on or off based on a comparison of a current time to at least one scheduled inactivity or at least one scheduled activity period, respectively, for the magnetoencephalography measurement device stored in the memory, the inactivity period allowing re-liquefaction of the helium gas flowing from the storage tank to the Dewar vessel by the cryocooler apparatus, when the Dewar vessel stores liquid helium and the storage tank stores helium gas.

In one embodiment of the invention, the sensors are Superconducting Quantum Interference Device (SQUID) sensors.

In one embodiment of the invention, the cryocooler apparatus is connected to a cryocooler body. The cryocooler body may be in gaseous communication with a compressor of the cryocooler apparatus via two lines.

In one embodiment of the invention, the lid comprises a plug for the mouth of the Dewar vessel.

In one embodiment of the invention, the plug comprises an intra-vessel portion and a supporting flange or lid, the intra-vessel portion comprising at least a first cooling stage and a second cooling stage of a cryocooler apparatus, the supporting flange supporting the plug assembly inside the mouth of the Dewar vessel and sealing the mouth of the Dewar vessel. The cryocooler body may be supported on top of the supporting flange.

In one embodiment of the invention, the control unit is separate from at least one computer communicatively connected to the sensor assembly, the at least one computer being used to gather measurement data from the sensor assembly and form an image of the gathered measurement data.

In one embodiment of the invention, the control unit switches the cryocooler on or off based on a comparison of a current time to at least one scheduled inactivity or at least one scheduled activity period for the magnetoencephalography measurement device stored in the memory, the inactivity period allowing re-liquefaction of the helium gas flowing from the storage tank to the Dewar vessel by the cryocooler.

According to a further aspect of the invention, the invention is a method, comprising: determining, by a control unit of a magnetoencephalography measurement device, an ending of a first scheduled inactivity period of the magnetoencephalography measurement device, the magnetoencephalography measurement device comprising liquid helium in a Dewar vessel, the liquid helium cooling an assembly of sensors of the magnetoencephalography measurement device to a superconductive temperature, the Dewar vessel being in gaseous communication with a storage tank for boiled helium; switching, by the control unit, a cryocooler apparatus of the magnetoencephalography measurement device off, in response to the determining of the ending of the first scheduled inactivity period, the cryocooler apparatus being suspended inside the Dewar vessel, a lid sealing the Dewar vessel and comprising an orifice allowing gaseous communication between the storage tank and the Dewar vessel; allowing a boiling of helium in the Dewar vessel during an activity period of the magnetoencephalography measurement device; pumping the boiled helium to the storage tank using a compressor activated by the control unit; performing at least one measurement using the magnetoencephalography measurement device; determining, by the control unit, a starting of a second scheduled inactivity period of the magnetoencephalography measurement device; and switching, by the control unit, the cryocooler on, in response to the determining of the starting of the second scheduled inactivity period, the first inactivity period and the second inactivity period allowing re-liquefaction of the helium flowing from the storage tank to the Dewar vessel by the cryocooler.

According to a further aspect of the invention, the invention is a computer program comprising code adapted to cause the following when executed on a data-processing system: determining, by a control unit of a magnetoencephalography measurement device, an ending of a first scheduled inactivity period of the magnetoencephalography measurement device, the magnetoencephalography measurement device comprising liquid helium in a Dewar vessel, the liquid helium cooling an assembly of sensors of the magnetoencephalography measurement device to a superconductive temperature, the Dewar vessel being in gaseous communication with a storage tank for boiled helium; switching, by the control unit, a cryocooler apparatus of the magnetoencephalography measurement device off, in response to the determining of the ending of the first scheduled inactivity period, the cryocooler apparatus being suspended inside the Dewar vessel, a lid sealing the Dewar vessel and comprising an orifice allowing gaseous communication between the storage tank and the Dewar vessel; allowing a boiling of helium in the Dewar vessel during an activity period of the magnetoencephalography measurement device; pumping the boiled helium to the storage tank using a compressor activated by the control unit; performing at least one measurement using the magnetoencephalography measurement device; determining, by the control unit, a starting of a second scheduled inactivity period of the magnetoencephalography measurement device; and switching, by the control unit, the cryocooler on, in response to the determining of the starting of the second scheduled inactivity period, the first inactivity period and the second inactivity period allowing re-liquefaction of the helium flowing from the storage tank to the Dewar vessel by the cryocooler.

According to a further aspect of the invention, the invention is a helium recirculation system, comprising: a plug assembly comprising an intra-vessel portion and a supporting flange, the intra-vessel portion comprising a first cooling stage and a second cooling stage of a cryocooler for cooling a Dewar vessel, the supporting flange being suitable for supporting the plug assembly inside a mouth of the Dewar vessel and suitable for sealing the mouth of the Dewar vessel, the supporting flange comprising an orifice allowing a flow of helium gas from a storage tank to the Dewar vessel and allowing pumping of boiled helium gas to the storage tank from the Dewar vessel; a pipeline connected to the orifice from a first end and to the storage tank at the second end, the pipeline comprising a compressor for pumping helium gas from the Dewar vessel to the storage tank; the storage tank arranged to store helium gas; the compressor arranged to pump helium gas from the Dewar vessel to the storage tank; and an apparatus comprising at least one processor and a memory storing instructions that, when executed, cause the apparatus to switch the cryocooler on or off based on a comparison of a current time to at least one scheduled inactivity or at least one scheduled activity period for the magnetoencephalography measurement device stored in the memory, the inactivity period allowing re-liquefaction of helium flowing from the storage tank to the Dewar vessel.

According to a further aspect of the invention, the invention is an apparatus comprising: means for determining an ending of a first scheduled inactivity period of the magnetoencephalography measurement device, the magnetoencephalography measurement device comprising liquid helium in a Dewar vessel, the liquid helium cooling an assembly of sensors of the magnetoencephalography measurement device to a superconductive temperature, the Dewar vessel being in gaseous communication with a storage tank for boiled helium; means for switching a cryocooler apparatus of the magnetoencephalography measurement device off, in response to the determining of the ending of the first scheduled inactivity period, the cryocooler apparatus being suspended inside the Dewar vessel, a lid sealing the Dewar vessel and comprising an orifice allowing gaseous communication between the storage tank and the Dewar vessel; means for allowing a boiling of helium in the Dewar vessel during an activity period of the magnetoencephalography measurement device; means for pumping the boiled helium to the storage tank using a compressor activated by the control unit; means for performing at least one measurement using the magnetoencephalography measurement device; means for determining, by the control unit, a starting of a second scheduled inactivity period of the magnetoencephalography measurement device; and means for switching, by the control unit, the cryocooler on, in response to the determining of the starting of the second scheduled inactivity period, the first inactivity period and the second inactivity period allowing re-liquefaction of the helium flowing from the storage tank to the Dewar vessel by the cryocooler.

According to a further aspect of the invention, the invention is a computer program product comprising the computer program.

In one embodiment of the invention, the pressure controlling device is a pressure regulator.

In one embodiment of the invention, the lid comprises a plug of the Dewar vessel.

In one embodiment of the invention, the plug comprises a flange surrounding the first stage of the cryocooler apparatus, the flange supporting the plug in the mouth, the flange comprising the first orifice.

In one embodiment of the invention, the cryocooler apparatus comprises a first cooling stage and a second cooling stage. The cryocooler apparatus may comprise a liquefier.

In one embodiment of the invention, the cryocooler apparatus may be connected to a cryocooler body, which may be placed on the flange. The cryocooler body may comprise, for example, at least one of a rotating valve, a surge volume and a motor of the rotating valve.

In one embodiment of the invention, the method further comprises: suspending the cryocooler apparatus inside the Dewar vessel; sealing the Dewar vessel with a lid, the lid comprising an orifice allowing gaseous communication between the storage tank and the Dewar vessel.

In one embodiment of the invention, the Dewar vessel stores liquid helium to cool the assembly of sensors to a superconductive temperature.

In one embodiment of the invention, the Dewar vessel has a minimum level for liquid helium so that the Magnetoencephalography measurement device is ready for operation without adding liquid helium to the Dewar vessel or without a need to wait for further re-liquefaction of helium gas by the cryocooler apparatus.

In one embodiment of the invention, the Dewar vessel comprises a body portion, a neck portion with a mouth, the neck portion extending from the body portion, and a helmet portion formed in the body portion, the assembly of sensors being arranged around the helmet portion inside the Dewar vessel.

In one embodiment of the invention, the plug comprises an intra-vessel portion and a supporting flange, the intra-vessel portion comprises a first cooling stage and a second cooling stage of a cryocooler apparatus. The first cooling stage and the second cooling stage may cool and liquefy the helium in the Dewar vessel. The supporting flange may support the plug assembly inside the mouth of the Dewar vessel and seal the mouth of the Dewar vessel.

In one embodiment of the invention, the supporting flange comprises an orifice allowing a flow of helium gas from a storage tank to the Dewar vessel and allowing pumping of boiled helium gas to the storage tank from the Dewar vessel.

In one embodiment of the invention, the orifice opens into a hollow interior surrounded by a sleeve of insulating material, for example, foam. The sleeve of insulating material encircles or houses the first cooling stage and the second cooling stage of the cryocooler apparatus.

In one embodiment of the invention, the control unit switches the compressor on in response to the control unit switching the cryocooler apparatus off. In one embodiment of the invention, the control unit switches the compressor off in response to the control unit switching the cryocooler apparatus on.

In one embodiment of the invention, the storage tank is in gaseous communication with the Dewar vessel via a line connected to the orifice, the line may comprise a pressure controlling device.

In one embodiment of the invention, the magnetoencephalography measurement device comprises a compressor arranged to pump helium gas from the Dewar vessel to the storage tank. The compressor may be in gaseous communication with the Dewar vessel via a first line that permits pumping of boiled helium from the Dewar vessel by the compressor. The compressor may be in gaseous communication with the storage tank via a second line that permits flow of compressed gas from the compressor to the storage tank. The first line and the second line may be connected via a bypass line that permits a flow of helium gas from the storage tank to the Dewar vessel. The bypass line may have a pressure controlling device, which may control the pressure of the Dewar, for example, to have a pressure in range of 20 mbar (g)-100 mbar (g). The pressure controlling device may be a pressure regulator.

In one embodiment of the invention, the plug comprises the cryocooler apparatus, a first cooling stage and a second cooling stage of the cryocooler apparatus being suspended inside the Dewar vessel, the first cooling stage and the second cooling stage being in contact with Helium gas inside the Dewar vessel.

In one embodiment of the invention, the plug comprises a flange surrounding the cryocooler apparatus, the flange supporting the plug in the mouth, the flange comprising the first orifice.

In one embodiment of the invention, plug comprises a thermal insulator sleeve which surrounds the first cooling stage and the second cooling stage for at least the length of the first cooling stage and the second cooling stage.

In one embodiment of the invention, the cryocooler apparatus is suspended inside the Dewar vessel from a plurality of supports attached to an inner wall of the Dewar vessel, the plug further comprising two second orifices via which two lines connecting the cryocooler apparatus to a compressor of the cryocooler apparatus outside the Dewar vessel are lead.

In one embodiment of the invention, the memory comprises a database storing information on at least one scheduled activity period for the magnetoencephalography measurement device, the at least one scheduled activity period comprising at least one magnetoencephalography measurement for a patient.

In one embodiment of the invention, the memory comprises information on at least one scheduled inactivity period for the magnetoencephalography measurement device.

In one embodiment of the invention, the at least one scheduled inactivity period is between two predefined times-of-day.

In one embodiment of the invention, a sum of durations of the at least one scheduled activity period within a time period comprising the at least one scheduled activity period do not exceed a predefined threshold value, the threshold value being selected to maintain at least a minimum level of liquid helium in the Dewar vessel.

In one embodiment of the invention, the time period is between 6 hours and 24 hours.

In one embodiment of the invention, the storage tank and the compressor are placed outside a magnetically shielded room.

In one embodiment of the invention, the Dewar vessel comprises a radiation shield.

In one embodiment of the invention, the radiation shield comprises at least one thermal switch switchable between a connected position and a disconnected position, the thermal switch forming in the connected position a thermal coupling between a stage of the cryocooler apparatus inside the Dewar vessel and the radiation shield, the thermal switch in the disconnected position disconnecting the thermal coupling between the stage of the cryocooler apparatus and the radiation shield.

In one embodiment of the invention, the instructions, when executed, cause the control unit also to switch the at least one thermal switch on to a connected position, in response to switching the cryocooler apparatus on, and switch the at least one thermal switch off to a disconnected position, in response to switching the cryocooler apparatus off.

In one embodiment of the invention, the instructions, when executed, cause the control unit to switch the compressor on, in response to the control unit switching the cryocooler apparatus off.

In one embodiment of the invention, the instructions, when executed, cause the control unit to switch the compressor off, in response to the control unit switching the cryocooler apparatus on.

In one embodiment of the invention, the cryocooler apparatus inside the Dewar vessel comprises a first cooling stage and the second cooling stage of a cryocooler. A cryocooler body comprising a rotating valve, a surge volume and a motor of the rotating valve may be placed outside the Dewar vessel on top of the plug.

In one embodiment of the invention, the cryocooler comprises a Gifford-McMahon cryocooler.

In one embodiment of the invention, the cryocooler comprises a pulse-tube cryocooler.

In one embodiment of the invention, the computer program is stored on a non-transitory computer readable medium. The non-transitory computer readable medium may be, but is not limited to, a removable memory card, a removable memory module, a magnetic disk, an optical disk, a holographic memory or a magnetic tape. A removable memory module may be, for example, a USB memory stick, a PCMCIA card or a smart memory card.

In one embodiment of the invention, an apparatus comprising at least one processor and at least one memory including computer program code, the at least one memory and the computer program code are configured to, with the at least one processor, cause the apparatus at least to perform a method according to any of the method steps.

The embodiments of the invention described hereinbefore may be used in any combination with each other. Several of the embodiments may be combined together to form a further embodiment of the invention. A method, a magnetoencephalography measurement device, a computer program or a computer program product to which the invention is related may comprise at least one of the embodiments of the invention described hereinbefore.

It is to be understood that any of the above embodiments or modifications can be applied singly or in combination to the respective aspects to which they refer, unless they are explicitly stated as excluding alternatives.

The benefits of the invention are related to a reduced use of helium by a MEG device and to improved MEG measurement quality due to reduced electromagnetic noise.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE EMBODIMENTS

Reference will now be made in detail to the embodiments of the present invention, examples of which are illustrated in the accompanying drawings.

Figure 1:
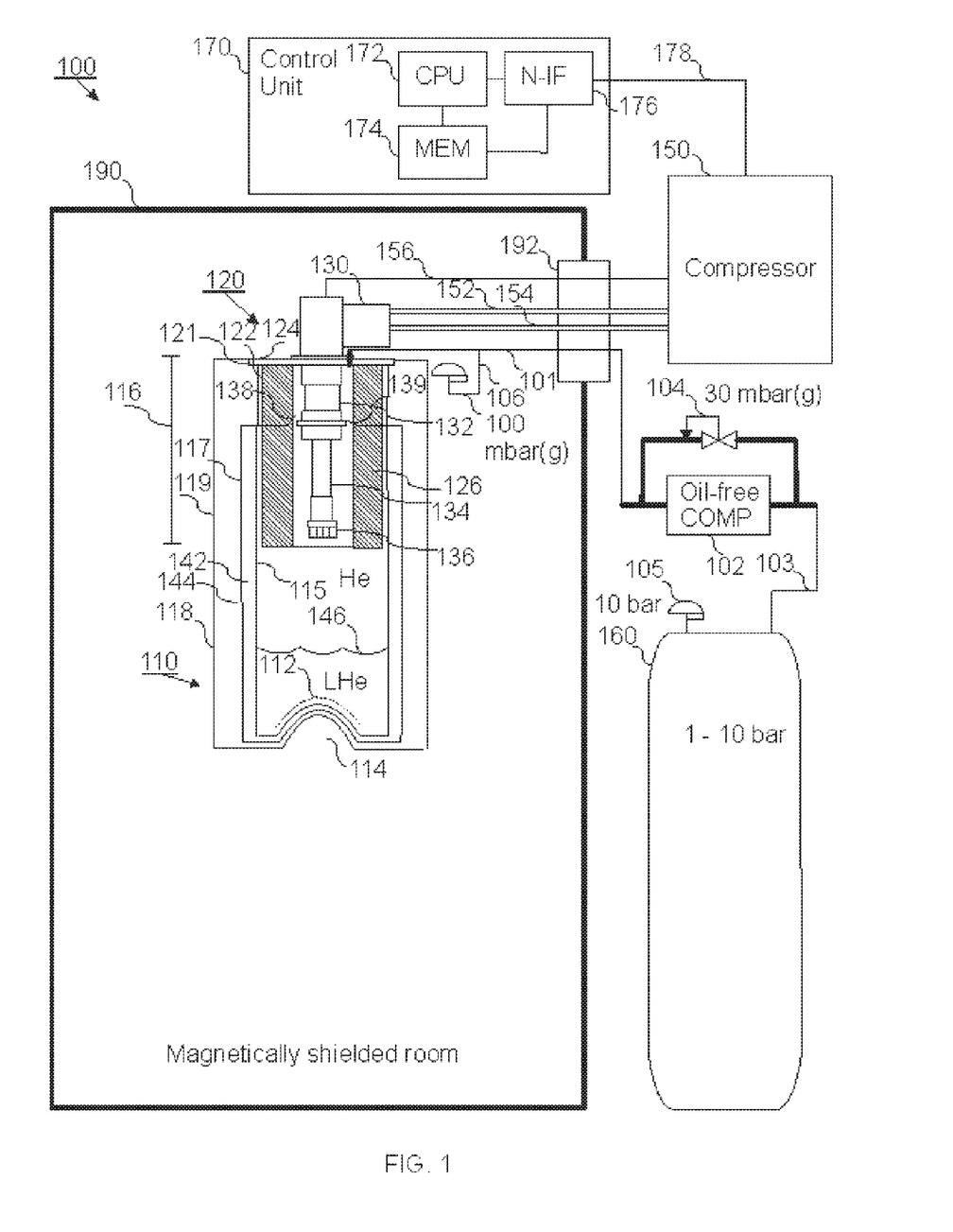
FIG. 1 illustrates a magnetoencephalography measurement device comprising a storage tank for boiled helium and a helium liquefier arranged in a neck of a Dewar vessel of the magnetoencephalography measurement device in one embodiment of the invention.

FIG. 1 illustrates a magnetoencephalography measurement device comprising a storage tank for boiled helium and a helium liquefier arranged in a neck of a Dewar vessel of the magnetoencephalography measurement device in one embodiment of the invention.

In FIG. 1 there is illustrated a cross-section of a magnetoencephalography measurement device 100. The magnetoencephalography measurement device comprises an assembly 112, in other words, an array 112 of Superconducting Quantum Interference Devices (SQUIDs) which are magnetic sensors. The SQUID sensors require a superconductive temperature to operate. Therefore, sensor assembly 112 is cooled using Liquid Helium (LHe) which has a boiling point of 4.2 Kelvins. Sensor assembly 112 is placed inside a Dewar vessel 110. Sensor assembly is kept below a surface 146 of liquid helium illustrated in FIG. 1. Dewar vessel 110 comprises a neck portion 116 and a body portion 118. Dewar vessel 110 also comprises a helmet portion 114 formed in body portion 118. Sensor assembly 112 is arranged around helmet portion 114 inside Dewar vessel 110. Dewar vessel 110 has an inner wall 115 which is in contact with the liquid or gaseous helium inside Dewar vessel 110. Dewar vessel has an outer wall 119. Between inner wall 115 and outer wall 119 there is mounted an insulating thermal radiation shield 117. Radiation shield 117 is mounted so that between inner wall 115 and radiation shield 117 there is an inner vacuum space 142. Similarly, between outer wall 119 and radiation shield 117 there is an outer vacuum space 144.

In FIG. 1 there is shown a plug assembly 120. Plug assembly 120 comprises a supporting flange 124 which supports plug assembly 120 on a mouth 121 of a neck portion 116 of Dewar vessel 110. A supporting flange 124 seals mouth 121 in neck portion 116. Supporting flange 124 may be a lid 124 of Dewar vessel 110. Plug assembly 120 comprises a cryocooler 130 mounted in supporting flange 124. Plug assembly comprises an intra-vessel portion 122 which is inserted into Dewar vessel 110 up to supporting flange 124. Intra-vessel portion 122 comprises a first cooling stage 132, a second cooling stage 134 and a liquefier 136 of cryocooler 130. Intra-vessel portion 122 comprises a plug 126 made of thermally insulating material arranged to house first cooling stage 132, second cooling stage 134 and liquefier 136 of cryocooler 130. Supporting flange 124 has an orifice (not shown) allowing a flow of helium gas that flows from a storage tank 160 into Dewar vessel 110 due to a pressure in storage tank 160 exceeding the pressure in Dewar vessel 110. The pressure in Dewar vessel 110 is kept, for example, at 30 mbar (g) which means the pressure is kept 30 mbar above the atmospheric pressure. The pressure in storage tank 160 is kept, for example, between 1 bar and 10 bars. The orifice allows pumping of helium gas that has boiled in Dewar vessel 110 back to storage tank 160 by means of an oil-free compressor 102. The orifice is in gaseous communication with storage tank 160 via a pipe 101, oil-free compressor 102 and a pipe 103. The orifice is also in gaseous communication with storage tank 160 via pipe 101, a pressure regulator 104, which keeps pressure in Dewar vessel 110, for example, above 30 mbar (g), and pipe 103. To pipe 101 there may be installed a pressure release valve 106, which prevents pressure in Dewar vessel 110 from exceeding 100 mbar (g), for example. To storage tank 160 there may be installed a pressure release valve 105, which prevents the pressure in storage tank 160 from exceeding, for example, 10 bars.

In one embodiment of the invention, a cryocooler body comprising, for example, a rotating valve (not shown), a surge volume (not shown), and a motor (not shown) of the rotating valve may be placed outside the Dewar vessel on top of the plug assembly 120.

In one embodiment of the invention, radiation shield 117 has a thermally conducting collar portion (not shown) which extends into plug 126. In one embodiment of the invention, the collar portion (not shown) is in thermal contact with at least two thermal switches, namely, a first thermal switch 138 and a second thermal switch 139. In FIG. 1 first thermal switch 138 is illustrated to be switched off, whereas switch 139 is illustrated to be switched on. First thermal switch 138 and second thermal switch 139 are illustrated to be in different positions for purposes of illustration only in FIG. 1. However, in one embodiment of the invention where first thermal switch 138 and second thermal switch 139 are utilized, the thermal switches are both in the same position. The at least two thermal switches may be made of metal and may have a form of a strip or spring. In one embodiment of the invention, the at least two thermal switches serve as a thermal bridges which connect radiation shield 117 thermally to first cooling stage 132 when the at least two thermal switches are switched on. When the at least two thermal switches are both switched off, there is no thermal contact between the collar portion of radiation shield 117 and first cooling stage 132. This prevents the flow of heat between radiation shield 117 and first cooling stage 132. In one embodiment of the invention, the flow of heat between radiation shield 117 and first cooling stage 132 is prevented by switching first thermal switch 138 and second thermal switch 139 off when cryocooler 130 is switched off. This has the effect that when cryocooler is switched off heat is not conducted via the cryocooler first stage to the radiation shield 117. On the other hand, when cryocooler 130 is switched on and first thermal switch 138 and second thermal switch 139 are switched on, cryocooler 130 cools radiation shield 117 via first cryocooler stage 132, first thermal switch 138 and second thermal switch 139 and the collar portion of radiation shield 117.

In one embodiment of the invention, a thermal switch may be switched between on and off positions, for example, by means of an electromagnetic coil which bends the strip or spring that forms the thermal switch when electricity is connected to the electromagnetic coil.

In FIG. 1 there is illustrated a compressor 150 in gaseous communication with the cold-head via a first gas line 152 and a second gas line 154. Compressor 150 is used to compress a working gas such as, for example, pressurized Helium, for example, at 10 bar to 30 bar range. In one embodiment of the invention, cryocooler 130 is a Gifford-McMahon cryocooler in which case first gas line 152 may be a high-pressure line and second gas line 154 may be a low-pressure line. Compressor 150 supplies electrical power to cryocooler 130 via a power supply cable 156. In one embodiment of the invention, cryocooler 130 is a pulse tube cryocooler.

In FIG. 1 there is also illustrated a control unit 170 which comprises a memory 174 and at least one processor 172. Control unit 170 also comprises a control interface 176 which allows processor 172 to transmit control signals to compressor 150 via a communication channel 178. The compressor 150 may comprise a control circuit (not shown) which switches the actual working gas compression performed by compressor 150 on or off based on control signals received from control unit 170 via communication channel 178. The control signals may be used to switch compressor 150 and cryocooler 130 on or off. Control unit 170 may also have a communication channel (not shown), which is connected to control interface 176, to allow transmission of control signals to oil-free compressor 102 to switch oil-free compressor 102 between on and off state.

Memory 174 stores instructions that, when executed, cause control unit 170 to switch cryocooler 130 and compressor 150 on or off based on a comparison of a current time to at least one scheduled inactivity or activity period for the magnetoencephalography measurement device stored in the memory, the inactivity period allowing re-liquefaction of helium pumped from the storage tank to the Dewar vessel. The current time may be obtained from an operating system of control unit 170 stored in memory 174. When cryocooler 130 is switched off, oil-free compressor 102 is switched on by control unit 170.

Memory 174 may store a schedule of future periods when magnetoencephalography measurement device 100 is active and used to perform measurements or inactive and not used. During periods of inactivity cryocooler 130 may be operated without causing disturbance to the magnetoencephalography measurements.

The starting point in FIG. 1 is that control unit 170 determines an ending of a first scheduled inactivity period of a magnetoencephalography measurement device. The control unit 170 switches the cryocooler 130 of magnetoencephalography measurement device 100 and a compressor 150 of the cryocooler 130 off, in response to the determining of the ending of the first scheduled inactivity period. The control unit 170 switches oil-free compressor 102 on. Oil-free compressor 102, due to being placed outside the magnetically shielded room, does not cause significant interference to sensor assembly 112 of MEG device 100. The switching of the cryocooler off allows boiling of helium in Dewar vessel 110 during an activity period of the magnetoencephalography measurement device. The boiled helium is pumped with oil-free compressor 102 to storage tank 160. During the activity period, at least one measurement is performed using the magnetoencephalography measurement device. Thereupon, control unit 170 determines a starting of a second scheduled inactivity period of the magnetoencephalography measurement device and switches cryocooler 130 and compressor 150 on, in response to the determining of the starting of the second scheduled inactivity period during which, the liquefier, connected to the second stage of the cryocooler, liquefies the helium gas flowing to the Dewar from the storage tank. At the same time oil-free compressor 102 may be switched off by control unit 170.

In FIG. 1 Dewar vessel 110 comprising sensor assembly 112 and plug assembly 120 are mounted inside a magnetically shielded room 190 while control unit 170, compressor 150, oil-free compressor 102 and storage tank 160 are placed outside magnetically shielded room 190.

As part of magnetoencephalography measurement device there may be a user-interface computer communicatively connected to each sensor in sensor assembly 112. The user-interface computer may be arranged to form MEG measurement images from data provided by sensor assembly 112. The user-interface computer is not shown for clarity purposes.

Figure 2:
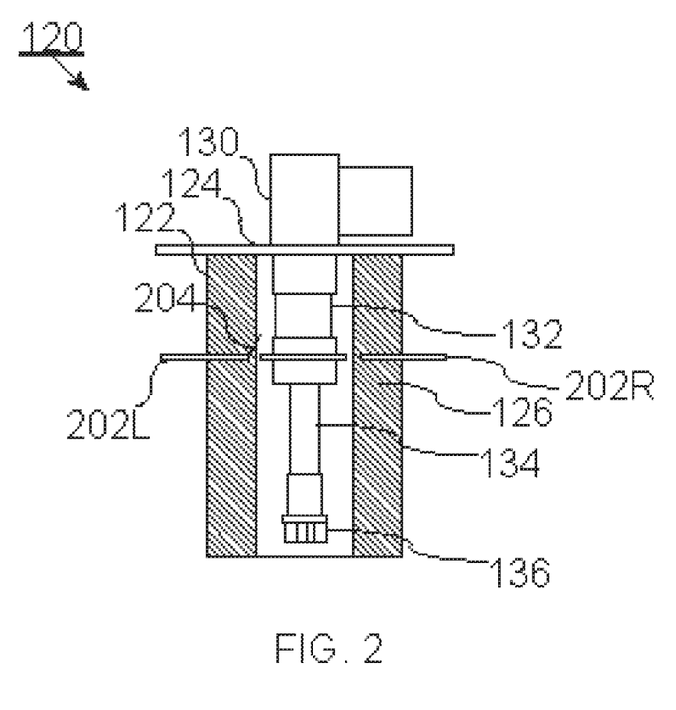
FIG. 2 illustrates plug assembly comprising a helium liquefier in one embodiment of the invention.

FIG. 2 illustrates plug comprising a helium liquefier in one embodiment of the invention. In FIG. 2 there is illustrated plug assembly 120 of FIG. 1.

In FIG. 2 there is shown a cross-section of a plug assembly 120. Plug assembly 120 comprises an intra-vessel portion 122 and a supporting flange 124. Supporting flange 124 may also be a lid 124 of Dewar vessel 110. The intra-vessel portion 122 comprises a first cooling stage 132, a second cooling stage 134 and a liquefier 136 of a cryocooler 130. Intra-vessel portion 122 may comprise a plug 126, which may be made of foam, arranged to house first cooling stage 132, second cooling stage 134 and liquefier 136 of cryocooler 130. Supporting flange 124 supports plug assembly 120 on neck portion 116 of Dewar vessel 110. Plug 126 may also comprise a cavity for first cooling stage 132, second cooling stage 134 and liquefier 136 of cryocooler 130. In FIG. 2 there is illustrated a collar portion 202L, 202R of radiation shield 117. The collar portion may be an annular plate that encircles first cooling stage 132. In FIG. 2 the collar portion is illustrated as a left part 202L and a right part 202R. There is also illustrated a single thermal switch 204 which is switched off.

Figure 3:
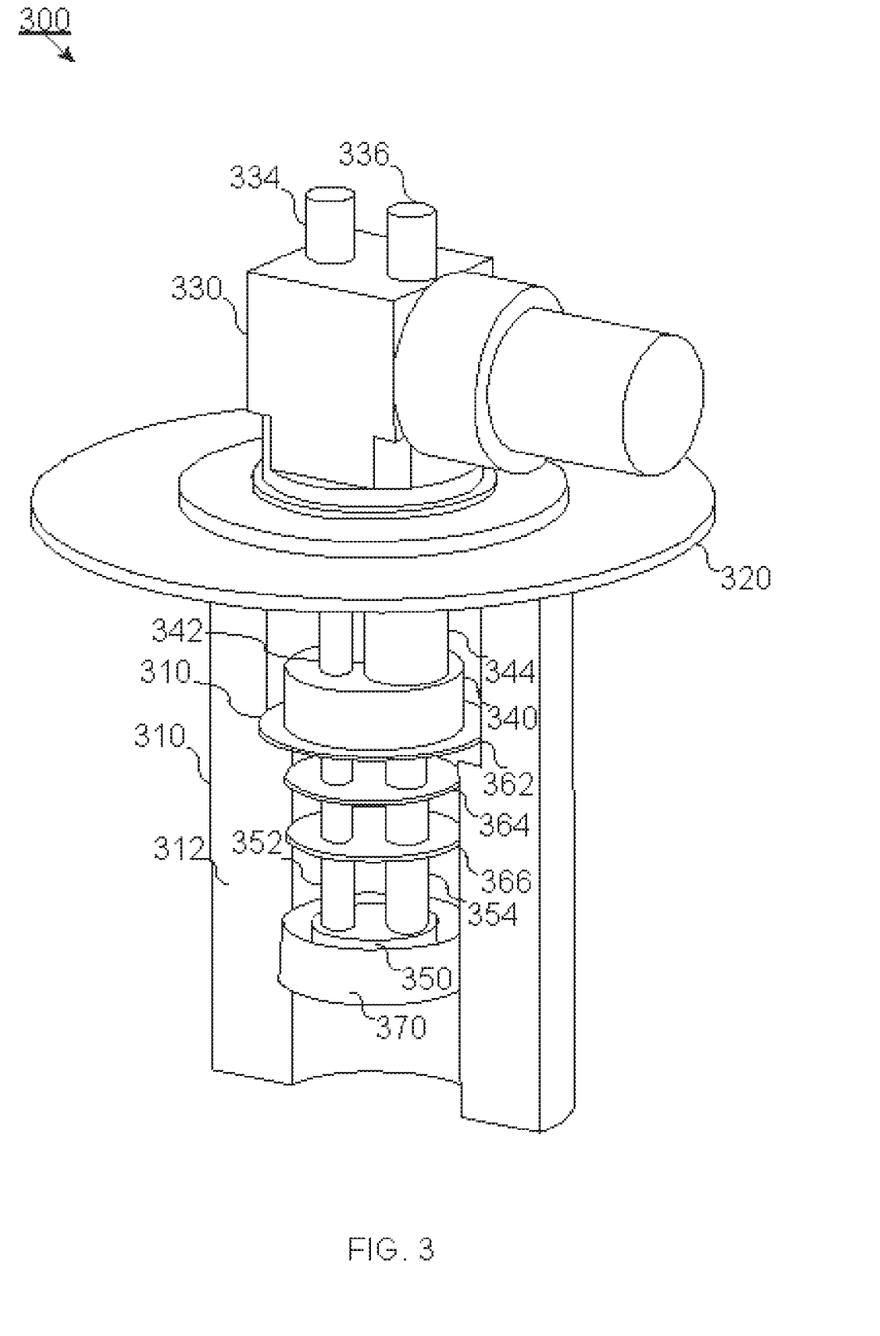
FIG. 3 illustrates three-dimensionally a plug assembly comprising a helium liquefier in one embodiment of the invention.

FIG. 3 illustrates three-dimensionally a plug assembly comprising a helium liquefier in one embodiment of the invention.

In FIG. 3 there is illustrated an intra-vessel portion 310 of a plug assembly 300. There is illustrated a supporting flange 320 arranged between intra-vessel portion 310 and an extra-vessel portion, which comprises a cryocooler 330, of plug assembly 300. In FIG. 3 the cryocooler is a pulse tube cryocooler. Supporting flange 320 allows plug assembly 300 to rest on a neck portion of a Dewar vessel. Flange 320 also has an inlet and an outlet (not shown) for helium. Cryocooler 330 has a first inlet/outlet 334 and a second inlet/outlet for working gas such as, for example, pressurized helium. Intra vessel portion 312 comprises a sleeve, for example, of polystyrene foam 312 which may have a width between 15 cm and 5 cm depending on an inner diameter of the neck of the Dewar vessel to which the plug assembly is mounted. There is an orifice (not shown) arranged to open into space surrounded by sleeve 312. Inside sleeve 312 there is placed a liquefier 370. To liquefier 370 there is thermally coupled a second stage heat exchanger 350. Second stage heat exchanger 350 is thermally coupled to a second stage pulse tube 352 and a second stage regenerator 354. To the second stage pulse tube 352 and the second stage regenerator 354 is thermally coupled a first stage heat exchanger 340. First stage heat exchanger 340 is thermally coupled to a first stage pulse tube 342 and a second stage regenerator 344, which are thermally coupled to the cryocooler 330. First stage heat exchanger 340 has a radiation shield plate 310 which prevents thermal radiation from crossing an otherwise empty space between first stage heat exchanger 340 and sleeve 312. Similarly, second stage pulse tube 352 and second stage regenerator 354 have radiation shield plates 364 and 366 which prevent thermal radiation toward liquid helium in an otherwise empty space between second stage pulse tube 352, second stage regenerator 354 and sleeve 312. Surfaces of sleeve 312, which face the inside surfaces of neck portion 118 of Dewar vessel 110, may be covered with superinsulation to seal the foam surface.

Figure 4:
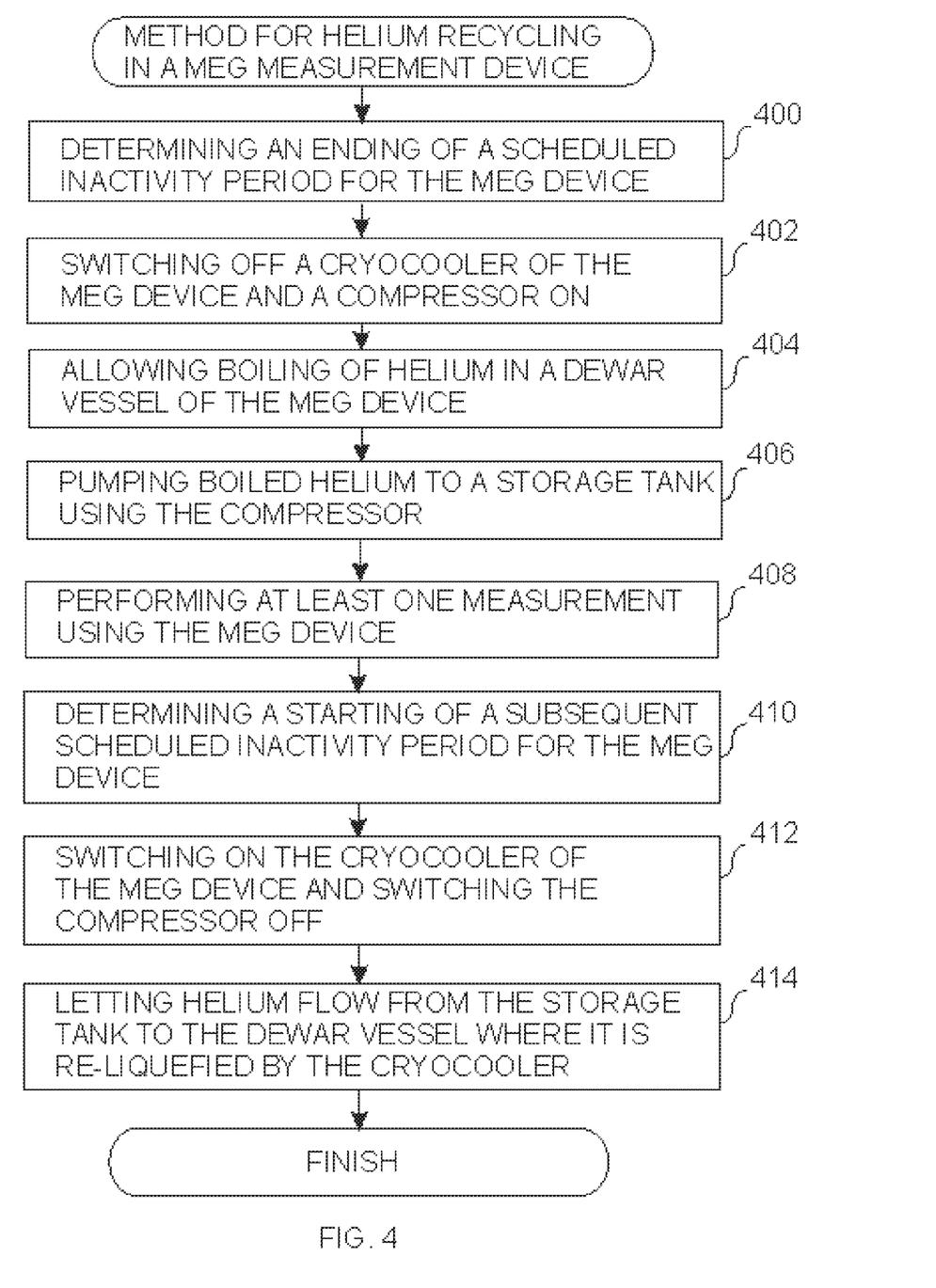
FIG. 4 is a flow chart illustrating a method for helium recycling in a magnetoencephalography measurement device in one embodiment of the invention.

FIG. 4 is a flow chart illustrating a method for helium recycling in a magnetoencephalography measurement device in one embodiment of the invention.

At step 400 there is determined an ending of a first scheduled inactivity period of a MEG measurement device. The determination may be carried out by a control unit of the MEG device. The MEG device may comprise liquid helium in a Dewar vessel. The liquid helium cools an assembly of sensors of the magnetoencephalography measurement device to a superconductive temperature. The Dewar vessel may have a storage tank for boiled helium in gaseous communication with the Dewar vessel. The gaseous communication may be implemented via helium supply lines between the storage tank and the Dewar vessel.

At step 402 a cryocooler of the MEG device is switched off, in response to the determining of the ending of the first scheduled inactivity period. The switching off may be performed by the control unit, in response to the determining of the ending of the first scheduled inactivity period. A first cooling stage and a second cooling stage of the cryocooler may be suspended inside the Dewar vessel in a plug assembly. A compressor may be switched on to pump boiled helium to the storage tank. The compressor may be switched on by the control unit.

At step 404 the MEG device allows boiling of helium in the Dewar vessel during an activity period of the MEG device. The boiling is allowed in response to switching off the cryocooler.

At step 406 a compressor runs to pump the boiled helium to the storage tank. The compressor may be periodically activated by the control unit or activated by the control unit in response to switching the cryocooler off by the control unit. The compressor may also be activated, by the control unit, in response to the pressure of helium gas in the Dewar vessel exceeding a predefined threshold value. The pressure may be determined using a pressure measuring device communicatively connected to the control unit.

At step 408 at least one measurement is performed using the MEG measurement device.

At step 410 there is determined a starting of a second scheduled inactivity period of the MEG measurement device. The determination may be performed by the control unit.

At step 412 the cryocooler is switched on and the compressor may be switched off, in response to the determining of the starting of the second scheduled inactivity period. The cryocooler may be switched on by the control unit. The compressor may be switched off by the control unit.

At step 414 the helium is let to flow from the storage tank to the Dewar, where it is re-liquefied by the cryocooler. The flow of helium to from the storage tank to the Dewar may be due to a higher pressure maintained in the storage tank.

The method steps may be performed in the order of numbering.

The embodiments of the invention described hereinbefore in association with FIGS. 1, 2, 3 and 4, and the summary of the invention may be used in any combination with each other. Several of the embodiments may be combined together to form a further embodiment of the invention.

The exemplary embodiments of the invention can be included within any suitable device, for example, including any suitable servers, workstations, PCs, lap-top computers, PDAs, Internet appliances, handheld devices, cellular telephones, wireless devices, other devices, and the like, capable of performing the processes of the exemplary embodiments, and which can communicate via one or more interface mechanisms, including, for example, Internet access, telecommunications in any suitable form (for instance, voice, modem, and the like), wireless communications media, one or more wireless communications networks, cellular communications networks, 3G communications networks, 4G communications networks, Public Switched Telephone Network (PSTNs), Packet Data Networks (PDNs), the Internet, intranets, a combination thereof, and the like.

It is to be understood that the exemplary embodiments are for exemplary purposes, as many variations of the specific hardware used to implement the exemplary embodiments are possible, as will be appreciated by those skilled in the hardware art(s). For example, the functionality of one or more of the components of the exemplary embodiments can be implemented via one or more hardware devices, or one or more software entities such as modules.

The exemplary embodiments can store information relating to various processes described herein. This information can be stored in one or more memories, such as a hard disk, optical disk, magneto-optical disk, RAM, and the like. One or more databases can store the information regarding cyclic prefixes used and the delay spreads measured. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be implemented by the preparation of one or more application-specific integrated circuits or by interconnecting an appropriate network of conventional component circuits, as will be appreciated by those skilled in the electrical art(s).

As stated above, the components of the exemplary embodiments can include computer readable medium or memories according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present inventions have been described in connection with a number of exemplary embodiments, and implementations, the present inventions are not so limited, but rather cover various modifications, and equivalent arrangements, which fall within the purview of prospective claims.

The embodiments of the invention described hereinbefore in association with the figures presented and the summary of the invention may be used in any combination with each other. Several of the embodiments may be combined together to form a further embodiment of the invention.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A magnetoencephalography measurement device, comprising:
   an assembly of a plurality of sensors placed inside a Dewar vessel;
   the Dewar vessel, when in use, storing liquid helium to cool the assembly of sensors to a superconductive temperature, the Dewar vessel comprising a body portion, a mouth, and a helmet portion formed in the body portion for receiving a patient's head, the assembly of sensors being arranged around the helmet portion inside the Dewar vessel;
   a cryocooler apparatus suspended inside the Dewar vessel;
   a lid sealing the mouth, the lid comprising a first orifice allowing a flow of helium gas from a storage tank to the Dewar vessel and allowing pumping of boiled helium gas to the storage tank from the Dewar vessel, when the Dewar vessel stores liquid helium and the storage tank stores helium gas;
   the storage tank in gaseous communication with the Dewar vessel via a line connected to the first orifice, when the Dewar vessel stores liquid helium and the storage tank stores helium gas, the line comprising a pressure controlling device;
   a compressor for pumping helium gas from the Dewar vessel to the storage tank, when the Dewar vessel stores liquid helium and the storage tank stores helium gas;
   a control unit comprising at least one processor and a memory storing instructions that, when executed, cause the control unit to switch the cryocooler apparatus on or off based on a comparison of a current time to at least one scheduled inactivity or at least one scheduled activity period, respectively, for the magnetoencephalography measurement device stored in the memory, the inactivity period allowing re-liquefaction of the helium gas flowing from the storage tank to the Dewar vessel by the cryocooler apparatus, when the Dewar vessel stores liquid helium and the storage tank stores helium gas; and wherein a sum of durations of the at least one scheduled activity period within a time period comprising the at least one scheduled activity period do not exceed a predefined threshold value, the threshold value being selected to maintain at least a minimum level of liquid helium in the Dewar vessel.

2. The magnetoencephalography measurement device according to claim 1, wherein the lid comprises a plug for the mouth of Dewar vessel.

3. The magnetoencephalography measurement device according to claim 2, wherein the plug comprises the cryocooler apparatus, a first cooling stage and a second cooling stage of the cryocooler apparatus being suspended inside the Dewar vessel, the first cooling stage and the second cooling stage being in contact with helium gas inside the Dewar vessel.

4. The magnetoencephalography measurement device according to claim 3, wherein the plug comprises a flange surrounding the cryocooler apparatus, the flange supporting the plug in the mouth, the flange comprising the first orifice.

5. The magnetoencephalography measurement device according to claim 3, wherein the plug comprises a thermal insulator sleeve which surrounds the first cooling stage and the second cooling stage for at least the length of the first cooling stage and the second cooling stage.

6. The magnetoencephalography measurement device according to claim 1, wherein the cryocooler apparatus is suspended inside the Dewar vessel from a plurality of supports attached to an inner wall of the Dewar vessel, the lid further comprising two second orifices via which two lines connecting the cryocooler apparatus to a compressor of the cryocooler apparatus outside the Dewar vessel are lead.

7. The magnetoencephalography measurement device according to claim 1, wherein the memory comprises a database storing information on at least one scheduled activity period for the magnetoencephalography measurement device, the at least one scheduled activity period comprising at least one magnetoencephalography measurement for a patient.

8. The magnetoencephalography measurement device according to claim 1, wherein the memory comprises information on at least one scheduled inactivity period for the magnetoencephalography measurement device.

9. The magnetoencephalography measurement device according to claim 8, wherein the at least one scheduled inactivity period is between two predefined times-of-day.

10. The magnetoencephalography measurement device according to claim 9, wherein the time period is between 6 hours and 24 hours.

11. The magnetoencephalography measurement device according to claim 1, wherein the storage tank and the compressor are placed outside a magnetically shielded room.

12. The magnetoencephalography measurement device according to claim 1, wherein the Dewar vessel comprises a radiation shield.

13. The magnetoencephalography measurement device according to claim 12, wherein the radiation shield comprises at least one thermal switch switchable between a connected position and a disconnected position, the thermal switch forming in the connected position a thermal coupling between a stage of the cryocooler apparatus inside the Dewar vessel and the radiation shield, the thermal switch in the disconnected position disconnecting the thermal coupling between the stage of the cryocooler apparatus and the radiation shield.

14. The magnetoencephalography measurement device according to claim 13, wherein the instructions, when executed, cause the control unit also to switch the at least one thermal switch on to a connected position, in response to switching the cryocooler apparatus on, and switch the at least one thermal switch off to a disconnected position, in response to switching the cryocooler apparatus off.

15. The magnetoencephalography measurement device according to claim 1, wherein the instructions, when executed, cause the control unit to switch the compressor on, in response to the control unit switching the cryocooler off.

16. The magnetoencephalography measurement device according to claim 15, wherein the instructions, when executed, cause the control unit to switch the compressor off, in response to the control unit switching the cryocooler apparatus on.

17. A method comprising:
determining, by a control unit of a magnetoencephalography measurement device, an ending of a first scheduled inactivity period of the magnetoencephalography measurement device, the magnetoencephalography measurement device comprising liquid helium in a Dewar vessel, the liquid helium cooling an assembly of sensors of the magnetoencephalography measurement device to a superconductive temperature, the Dewar vessel being in gaseous communication with a storage tank for boiled helium;
switching, by the control unit, a cryocooler apparatus of the magnetoencephalography measurement device off, in response to the determining of the ending of the first scheduled inactivity period, the cryocooler apparatus being suspended inside the Dewar vessel, a lid sealing the Dewar vessel and comprising an orifice allowing gaseous communication between the storage tank and the Dewar vessel;
allowing a boiling of helium in the Dewar vessel during an activity period of the magnetoencephalography measurement device;
pumping the boiled helium to the storage tank using a compressor activated by the control unit;
performing at least one measurement using the magnetoencephalography measurement device;
determining, by the control unit, a starting of a second scheduled inactivity period of the magnetoencephalography measurement device;
switching, by the control unit, the cryocooler apparatus on, in response to the determining of the starting of the second scheduled inactivity period, the first inactivity period and the second inactivity period allowing re-liquefaction of the helium flowing from the storage tank to the Dewar vessel by the cryocooler apparatus; and
wherein a sum of durations of the at least one scheduled activity period within a time period comprising the at least one scheduled activity period do not exceed a predefined threshold value, the threshold value being selected to maintain at least a minimum level of liquid helium in the Dewar vessel.

18. A computer program comprising code adapted to cause the following when executed on a data-processing system:
determining, by a control unit of a magnetoencephalography measurement device, an ending of a first scheduled inactivity period of the magnetoencephalography measurement device, the magnetoencephalography measurement device comprising liquid helium in a Dewar vessel, the liquid helium cooling an assembly of sensors of the magnetoencephalography measurement device to a superconductive temperature, the Dewar vessel being in gaseous communication with a storage tank for boiled helium;

switching, by the control unit, a cryocooler apparatus of the magnetoencephalography measurement device off, in response to the determining of the ending of the first scheduled inactivity period, the cryocooler apparatus being suspended inside the Dewar vessel, a lid sealing the Dewar vessel and comprising an orifice allowing gaseous communication between the storage tank and the Dewar vessel;

allowing a boiling of helium in the Dewar vessel during an activity period of the magnetoencephalography measurement device;

pumping the boiled helium to the storage tank using a compressor activated by the control unit;

performing at least one measurement using the magnetoencephalography measurement device;

determining, by the control unit, a starting of a second scheduled inactivity period of the magnetoencephalography measurement device;

switching, by the control unit, the cryocooler apparatus on, in response to the determining of the starting of the second scheduled inactivity period, the first inactivity period and the second inactivity period allowing re-liquefaction of the helium flowing from the storage tank to the Dewar vessel by the cryocooler apparatus; and wherein a sum of durations of the at least one scheduled activity period within a time period comprising the at least one scheduled activity period do not exceed a predefined threshold value, the threshold value being selected to maintain at least a minimum level of liquid helium in the Dewar vessel; and wherein said computer program is stored on a non-transitory computer readable medium.

* * * * *